(12) United States Patent
Zumbrum

(10) Patent No.: US 11,584,571 B2
(45) Date of Patent: *Feb. 21, 2023

(54) VESSEL CLOSURES AND METHODS FOR USING AND MANUFACTURING SAME

(71) Applicant: Sartorius Stedim North America Inc., Bohemia, NY (US)

(72) Inventor: Michael A. Zumbrum, New Oxford, PA (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/011,148

(22) Filed: Sep. 3, 2020

(65) Prior Publication Data

US 2020/0399029 A1    Dec. 24, 2020

Related U.S. Application Data

(63) Continuation of application No. 16/015,256, filed on Jun. 22, 2018, now Pat. No. 10,773,863, which is a
(Continued)

(51) Int. Cl.
*A61M 39/10* (2006.01)
*B65D 47/00* (2006.01)
(Continued)

(52) U.S. Cl.
CPC ........... *B65D 47/00* (2013.01); *A61M 39/105* (2013.01); *B65D 55/00* (2013.01); *B67D 1/0807* (2013.01);
(Continued)

(58) Field of Classification Search
CPC ........... F16L 23/16; F16L 23/18; F16L 23/22; Y10T 137/85938; A61M 39/105
See application file for complete search history.

(56) References Cited

U.S. PATENT DOCUMENTS

| | | | |
|---|---|---|---|
| 553,734 | A | 1/1896 | Iredale |
| 1,438,899 | A | 12/1922 | Cassidy |
| 1,577,539 | A | 3/1926 | Polk |
| 1,834,085 | A | 12/1931 | Bloom |
| 2,186,908 | A | 1/1940 | Page et al. |
| 2,191,495 | A | 2/1940 | Nesset |

(Continued)

FOREIGN PATENT DOCUMENTS

| | | |
|---|---|---|
| CN | 102218226 A | 10/2011 |
| DE | 3505492 A1 | 8/1986 |

(Continued)

OTHER PUBLICATIONS

"How it's made: Silicone Hoses manufacturing by Viper Performance" (Viperperformanceuk) Oct. 1, 2014, Available Online at <https://www.youtube.com/watch?v=iuO0TdzHnWo> 5:30-6:30, 1 page.

(Continued)

*Primary Examiner* — Kevin F Murphy
(74) *Attorney, Agent, or Firm* — Womble Bond Dickinson (US) LLP

(57) ABSTRACT

A fluid transfer hub has a first vessel closure, a second vessel closure, a gasket arranged between the first vessel closure and the second vessel closure, and a clamp at least partially surrounding the first vessel closure, the second vessel closure, and the gasket. The first vessel closure has a first body, one or more apertures extending axially through the first body, one or more first inserts extending axially through the one or more apertures, and a cast seal disposed within the first body and surrounding each first insert. The second vessel closure has a second body, one or more apertures extending axially through the second body, one or more second inserts extending axially through the one or more apertures, and a cast seal disposed within the second body and surrounding each second insert.

20 Claims, 9 Drawing Sheets

Related U.S. Application Data continuation-in-part of application No. 14/128,259, filed as application No. PCT/US2011/041462 on Jun. 22, 2011, now Pat. No. 10,006,567.

(51) Int. Cl.

| | | |
|---|---|---|
| *B65D 55/00* | (2006.01) | |
| *B67D 3/00* | (2006.01) | |
| *B67D 1/08* | (2006.01) | |
| *F16L 23/16* | (2006.01) | |
| *B65D 53/06* | (2006.01) | |
| *B65D 51/24* | (2006.01) | |
| *B65D 47/06* | (2006.01) | |
| *B65D 41/04* | (2006.01) | |
| *B65D 51/00* | (2006.01) | |

(52) U.S. Cl.
CPC ............ *B67D 3/0061* (2013.01); *F16L 23/16* (2013.01); *B65D 41/0435* (2013.01); *B65D 47/06* (2013.01); *B65D 51/002* (2013.01); *B65D 51/24* (2013.01); *B65D 53/06* (2013.01)

(56) References Cited

U.S. PATENT DOCUMENTS

| | | |
|---|---|---|
| 2,226,312 A | 12/1940 | Kuhns |
| 2,439,572 A | 4/1948 | Levin |
| 2,460,542 A | 2/1949 | Smith |
| 2,744,661 A | 5/1956 | Davis |
| 3,130,260 A | 4/1964 | Gray |
| 3,276,447 A | 10/1966 | Hamilton |
| 3,354,012 A | 11/1967 | Forman et al. |
| 3,360,008 A | 12/1967 | Papale et al. |
| 3,458,619 A | 7/1969 | Prochaska |
| 3,467,270 A | 9/1969 | Eady |
| 3,499,568 A | 3/1970 | Vinas Riera |
| 3,793,672 A | 2/1974 | Wetmore |
| 3,794,333 A | 2/1974 | Czernik et al. |
| 3,938,035 A | 2/1976 | Fletcher et al. |
| 4,032,311 A | 6/1977 | Bohmrich et al. |
| 4,045,860 A | 9/1977 | Winckler |
| 4,080,989 A | 3/1978 | Chapelsky et al. |
| 4,116,199 A | 9/1978 | Bryne |
| 4,165,814 A | 8/1979 | Seel |
| 4,174,743 A | 11/1979 | Beny et al. |
| 4,334,993 A | 6/1982 | Norton |
| 4,335,717 A | 6/1982 | Bujan et al. |
| 4,336,802 A | 6/1982 | Stone et al. |
| 4,360,776 A | 11/1982 | Bauman |
| 4,396,016 A | 8/1983 | Becker |
| 4,499,148 A | 2/1985 | Goodale et al. |
| 4,512,368 A | 4/1985 | Kamanika et al. |
| 4,581,012 A | 4/1986 | Brown et al. |
| 4,676,898 A | 6/1987 | Saxena |
| 4,700,861 A | 10/1987 | Neward |
| 4,701,159 A | 10/1987 | Brown et al. |
| 4,715,359 A | 12/1987 | Ryo |
| 4,784,299 A | 11/1988 | Stenger |
| 4,785,974 A | 11/1988 | Rudick et al. |
| 4,804,208 A * | 2/1989 | Dye .................... A61M 39/105 285/308 |
| 4,863,030 A | 9/1989 | Bayer et al. |
| 4,938,371 A | 7/1990 | Vercillo |
| 4,993,573 A | 2/1991 | Freidel et al. |
| 5,025,955 A | 6/1991 | Stenger |
| 5,052,105 A | 10/1991 | Mische et al. |
| D324,568 S | 3/1992 | Marken |
| 5,100,010 A | 3/1992 | Waters |
| 5,114,045 A | 5/1992 | Herpe |
| 5,197,895 A | 3/1993 | Stupecky |
| 5,219,185 A | 6/1993 | Oddenino |
| 5,245,955 A | 9/1993 | Husted |
| 5,250,041 A | 10/1993 | Folden et al. |
| 5,300,060 A | 4/1994 | Nelson |
| 5,350,080 A | 9/1994 | Brown et al. |
| 5,358,872 A | 10/1994 | Mussi et al. |
| 5,362,642 A | 11/1994 | Kern |
| 5,381,839 A | 1/1995 | Dowd |
| H1430 H | 4/1995 | Apel et al. |
| 5,441,197 A | 8/1995 | Gellert et al. |
| 5,476,116 A | 12/1995 | Price et al. |
| 5,478,119 A | 12/1995 | Dye |
| 5,492,531 A | 2/1996 | Post et al. |
| 5,505,495 A | 4/1996 | Godeau |
| 5,507,904 A | 4/1996 | Fisher et al. |
| 5,518,047 A | 5/1996 | Alexandrowski |
| 5,522,155 A | 6/1996 | Jones |
| 5,695,215 A | 12/1997 | Headley et al. |
| 5,733,452 A | 3/1998 | Whitlock |
| 5,839,471 A | 11/1998 | Yang |
| 5,988,422 A | 11/1999 | Vallot |
| 6,032,543 A | 3/2000 | Aarthun et al. |
| 6,039,718 A | 3/2000 | Niedospial, Jr. |
| 6,062,440 A | 5/2000 | Murray et al. |
| 6,071,005 A | 6/2000 | Ekambaram et al. |
| 6,095,356 A | 8/2000 | Rits |
| 6,158,484 A | 12/2000 | Greenlee |
| 6,165,362 A | 12/2000 | Nohren et al. |
| 6,179,823 B1 | 1/2001 | Niedospial |
| 6,223,938 B1 | 5/2001 | Pare et al. |
| 6,225,562 B1 | 5/2001 | Fujishita et al. |
| 6,234,545 B1 | 5/2001 | Babuder et al. |
| 6,290,265 B1 | 9/2001 | Warburton-Pitt et al. |
| 6,334,888 B1 | 1/2002 | Collas et al. |
| 6,340,033 B2 | 1/2002 | Paradis et al. |
| 6,354,636 B2 | 3/2002 | Matsuzawa et al. |
| 6,430,033 B1 | 8/2002 | Mitsui et al. |
| 6,499,618 B1 | 12/2002 | Leclerc et al. |
| 6,520,505 B1 | 2/2003 | Koegler et al. |
| 6,523,711 B1 | 2/2003 | Hughes et al. |
| 6,578,802 B1 | 6/2003 | Thier |
| 6,581,637 B2 | 6/2003 | Hamamoto et al. |
| 6,610,200 B1 | 8/2003 | Leijon et al. |
| 6,719,037 B2 | 4/2004 | Crook |
| 6,733,730 B1 | 5/2004 | Griffiths et al. |
| 6,779,575 B1 | 8/2004 | Arthun |
| 6,905,595 B2 | 6/2005 | Gebauer |
| 6,951,228 B2 * | 10/2005 | Steigerwalt ........... A61M 39/24 141/105 |
| 6,966,581 B2 | 11/2005 | Mastropaolo |
| 6,994,699 B2 | 2/2006 | Houwaert et al. |
| 7,087,047 B2 | 8/2006 | Kraus et al. |
| 7,093,859 B2 | 8/2006 | Warburton-Pitt et al. |
| 7,140,404 B2 | 11/2006 | Cupples et al. |
| 7,293,477 B2 | 11/2007 | Furey et al. |
| 7,306,583 B2 | 12/2007 | Goudaliez et al. |
| 7,350,833 B2 * | 4/2008 | Bongiorno .............. F16L 23/04 285/365 |
| 7,407,612 B2 | 8/2008 | Warburton-Pitt et al. |
| 7,497,130 B2 | 3/2009 | Woods et al. |
| 7,500,949 B2 | 3/2009 | Gottlieb et al. |
| 7,563,243 B2 | 7/2009 | Mendels |
| 7,686,037 B2 | 3/2010 | Krywitsky |
| 7,708,923 B1 | 5/2010 | Helicke et al. |
| 7,731,241 B2 | 6/2010 | Aoki et al. |
| 7,784,630 B2 | 8/2010 | Walsh |
| 7,874,467 B2 | 1/2011 | Pardes et al. |
| 7,931,859 B2 | 4/2011 | Mlodzinski et al. |
| 8,008,065 B2 | 8/2011 | Selker et al. |
| 8,025,271 B2 | 9/2011 | Kolodner et al. |
| 8,092,409 B2 | 1/2012 | Mros et al. |
| 8,196,614 B2 | 6/2012 | Kriheli |
| 8,235,067 B2 | 8/2012 | Gagne et al. |
| 8,281,672 B2 | 10/2012 | Lee et al. |
| 8,281,807 B2 | 10/2012 | Trombley et al. |
| 8,336,313 B2 | 12/2012 | McMasters et al. |
| 8,342,737 B2 | 1/2013 | Greller et al. |
| 8,372,058 B2 | 2/2013 | Schilp et al. |
| 8,505,396 B2 | 8/2013 | Zumbrum |
| 8,505,586 B2 | 8/2013 | Zumbrum |
| 8,524,174 B2 | 9/2013 | Yobas et al. |
| 8,562,572 B2 | 10/2013 | Proulx et al. |
| 8,573,424 B2 | 11/2013 | Dubs et al. |

(56) References Cited

U.S. PATENT DOCUMENTS

| | | |
|---|---|---|
| 8,690,120 B2 | 4/2014 | Hartnei, I et al. |
| 8,865,427 B2 | 10/2014 | Poo et al. |
| 8,871,317 B2 | 10/2014 | Cai et al. |
| 9,095,693 B2 | 8/2015 | Buisson |
| 9,211,364 B2 | 12/2015 | Croizat et al. |
| 9,227,046 B1 | 1/2016 | Douglas |
| 9,259,563 B2 | 2/2016 | Klingel et al. |
| 9,358,333 B2 | 6/2016 | Trombley et al. |
| 9,376,224 B2 | 6/2016 | Gonnelli et al. |
| 9,376,305 B2 | 6/2016 | Zumbrum |
| 9,526,886 B2 | 12/2016 | Mastri et al. |
| 9,528,632 B2 | 12/2016 | Glaun |
| 9,550,969 B2 | 1/2017 | Chotteau et al. |
| 9,597,732 B2 | 3/2017 | Lewis et al. |
| 9,675,520 B2 | 6/2017 | Rogers et al. |
| 9,700,844 B2 | 7/2017 | Schick |
| 9,706,793 B2 | 7/2017 | Hayakawa |
| 9,726,314 B2 | 8/2017 | Py |
| 9,771,629 B2 | 9/2017 | Soloway |
| 9,784,111 B2 | 10/2017 | Luo et al. |
| 9,802,172 B2 | 10/2017 | Janders et al. |
| 9,857,002 B2 | 1/2018 | Ott et al. |
| 9,901,729 B2 | 2/2018 | Vigna et al. |
| 9,907,728 B2 | 3/2018 | Kyle et al. |
| 9,926,185 B2 | 3/2018 | Davis et al. |
| 9,938,128 B2 | 4/2018 | Py et al. |
| 9,944,510 B2 | 4/2018 | Zumbrum |
| 9,975,753 B1 | 5/2018 | Zumbrum et al. |
| 9,987,508 B2 | 6/2018 | Cockerham et al. |
| 10,006,567 B2 | 6/2018 | Zumbrum |
| 10,486,959 B2 | 11/2019 | Zumbrum |
| 10,773,863 B2 * | 9/2020 | Zumbrum ............... F16L 23/16 |
| 11,319,201 B2 | 5/2022 | Zumbrum et al. |
| 2001/0015226 A1 | 8/2001 | Hamamoto et al. |
| 2001/0017161 A1 | 8/2001 | Paradis et al. |
| 2001/0035093 A1 | 11/2001 | Yokota |
| 2002/0162648 A1 | 11/2002 | Crook |
| 2002/0185186 A1 | 12/2002 | Juliar et al. |
| 2003/0052074 A1 | 3/2003 | Chang et al. |
| 2003/0208151 A1 | 11/2003 | Kraus et al. |
| 2004/0026265 A1 | 2/2004 | Nadanami et al. |
| 2004/0059178 A1* | 3/2004 | McCarthy ........... A61M 60/857 600/16 |
| 2004/0064086 A1 | 4/2004 | Gottlieb et al. |
| 2004/0099154 A1 | 5/2004 | Raschle |
| 2004/0260265 A1 | 12/2004 | Goudaliez et al. |
| 2005/0067367 A1 | 3/2005 | Carballido |
| 2005/0115917 A1 | 6/2005 | Odet et al. |
| 2005/0124935 A1 | 6/2005 | McMichael |
| 2005/0132821 A1 | 6/2005 | Furey et al. |
| 2005/0142315 A1 | 6/2005 | Desimone et al. |
| 2005/0167390 A1 | 8/2005 | Dubs et al. |
| 2005/0256461 A1 | 11/2005 | Difiore et al. |
| 2005/0267445 A1 | 12/2005 | Mendels |
| 2006/0010991 A1 | 1/2006 | Woods et al. |
| 2006/0086758 A1 | 4/2006 | Coles |
| 2006/0272432 A1 | 12/2006 | Belongia |
| 2007/0161970 A1* | 7/2007 | Spohn .................. A61M 5/007 604/533 |
| 2007/0193375 A1 | 8/2007 | Pandori et al. |
| 2007/0290004 A1 | 12/2007 | Lee et al. |
| 2008/0087626 A1 | 4/2008 | Tsai |
| 2008/0277926 A1 | 11/2008 | Inman et al. |
| 2008/0281200 A1 | 11/2008 | Voic et al. |
| 2009/0049988 A1 | 2/2009 | Meindl |
| 2009/0090689 A1 | 4/2009 | Walsh |
| 2009/0236374 A1 | 9/2009 | Pardes et al. |
| 2010/0065305 A1 | 3/2010 | Bernauer |
| 2010/0123094 A1 | 5/2010 | Zumbrum |
| 2010/0133459 A1 | 6/2010 | Zumbrum |
| 2010/0154569 A1 | 6/2010 | Guedon |
| 2010/0158759 A1 | 6/2010 | Olivier |
| 2010/0164176 A1 | 7/2010 | Beele |
| 2010/0183251 A1 | 7/2010 | Neltner et al. |
| 2010/0288382 A1 | 11/2010 | Levent et al. |
| 2010/0318069 A1 | 12/2010 | Hall et al. |
| 2011/0018206 A1 | 1/2011 | Beele |
| 2011/0121558 A1 | 5/2011 | Kanner |
| 2011/0155258 A1 | 6/2011 | Zumbrum |
| 2011/0155274 A1 | 6/2011 | Zumbrum |
| 2012/0064274 A1 | 3/2012 | Cai et al. |
| 2012/0074051 A1 | 3/2012 | Gebauer et al. |
| 2013/0304039 A1 | 11/2013 | Chung |
| 2014/0074015 A1 | 3/2014 | Mastri et al. |
| 2014/0076454 A1 | 3/2014 | Kjar |
| 2014/0103077 A1 | 4/2014 | Zumbrum |
| 2014/0135719 A1 | 5/2014 | Jaeb et al. |
| 2014/0137519 A1 | 5/2014 | Goodwin et al. |
| 2014/0190570 A1 | 7/2014 | Zumbrum |
| 2014/0191501 A1 | 7/2014 | Brugger et al. |
| 2014/0353878 A1 | 12/2014 | Driessen et al. |
| 2015/0080814 A1 | 3/2015 | Lambert et al. |
| 2015/0259085 A1 | 9/2015 | Malone |
| 2016/0114922 A1 | 4/2016 | Boira et al. |
| 2016/0195208 A1 | 7/2016 | Cassiday et al. |
| 2016/0199914 A1 | 7/2016 | Potter |
| 2016/0202101 A1 | 7/2016 | Sparks |
| 2016/0238324 A1 | 8/2016 | Butcher et al. |
| 2016/0311674 A1 | 10/2016 | Zumbrum |
| 2016/0361488 A1 | 12/2016 | Perrenoud |
| 2017/0021355 A1 | 1/2017 | Olivier et al. |
| 2017/0102089 A1 | 4/2017 | Griffin et al. |
| 2017/0167652 A1 | 6/2017 | Snyder et al. |
| 2017/0173495 A1 | 6/2017 | Valery et al. |
| 2017/0204989 A1 | 7/2017 | Burkhart et al. |
| 2017/0219134 A1 | 8/2017 | Kedor et al. |
| 2017/0239141 A1 | 8/2017 | Davis et al. |
| 2017/0306766 A1 | 10/2017 | Munzer |
| 2018/0163898 A1 | 6/2018 | Von Arb |
| 2018/0297753 A1 | 10/2018 | Zumbrum |
| 2019/0143093 A1 | 5/2019 | Zumbrum et al. |
| 2020/0180938 A1 | 6/2020 | Zumbrum et al. |
| 2021/0024338 A1 | 1/2021 | Zumbrum et al. |

FOREIGN PATENT DOCUMENTS

| | | |
|---|---|---|
| DE | 102014104334 A1 | 10/2015 |
| EP | 1591517 A1 | 11/2005 |
| EP | 2144589 A1 | 1/2010 |
| EP | 2802415 A1 | 11/2014 |
| EP | 2805737 A1 | 11/2014 |
| EP | 3206816 A1 | 8/2017 |
| EP | 3215286 A1 | 9/2017 |
| GB | 0781520 A | 8/1957 |
| JP | 2001-031126 A | 2/2001 |
| JP | 2003-125753 A | 5/2003 |
| JP | 2007-176537 A | 7/2007 |
| JP | 4466778 B1 | 5/2010 |
| JP | 2010-120250 A | 6/2010 |
| KR | 0116728 Y1 | 4/1998 |
| KR | 10-2001-0016728 A | 3/2001 |
| WO | 96/30274 A1 | 10/1996 |
| WO | 98/54568 A1 | 12/1998 |
| WO | 2005/084372 A2 | 9/2005 |
| WO | 2008/136720 A1 | 11/2008 |
| WO | 2010/008396 A2 | 1/2010 |
| WO | 2012/177250 A1 | 12/2012 |
| WO | 2013/072348 A1 | 5/2013 |
| WO | 2013/105966 A1 | 7/2013 |
| WO | 2015/084388 A1 | 6/2015 |
| WO | 2016/078800 A1 | 5/2016 |
| WO | 2016/091629 A1 | 6/2016 |
| WO | 2017/063623 A1 | 4/2017 |
| WO | 2017/082895 A1 | 5/2017 |
| WO | 2017/156240 A1 | 9/2017 |
| WO | 2018/117949 A1 | 6/2018 |
| WO | 2019/099406 A1 | 5/2019 |

OTHER PUBLICATIONS

"Saint-Gobain Biopharm C-Flex EZ Top container closures", Available Online at <http://www.biopharm.saint-gobain.com/en/products.asp?id=66>, Oct. 15, 2013.

(56) References Cited

OTHER PUBLICATIONS

Disposable Polyethylene Vent Cap, Coming Life Sciences Catalot, http://catalog2.corning.com/LifeSciences/en-US/Shopping/ProductsDetails.a-spx2pid . . . , known at least as early as Mar. 18, 2014, 2 pages.
European Search Report and Search Opinion received for EP Application No. 11868058.6, dated Dec. 18, 2014, 7 pages.
European Search Report and Search Opinion received for EP Application No. 18154629.2, dated Jun. 19, 2018, 5 pages.
European Search Report and Search Opinion received for EP Application No. 19181109, dated Oct. 16, 2019, 8 pages.
GE Healthcare Life Sciences, "Disposable Cellbag bioreactors for WAVE Bioreactor systems", Data file 28-9511-36 AF, Sweden, Jun. 2012, pp. 1-12.
Injection-Molded Silicone Stoppers Platinum Cured, AdvantaPure, known at least as early as Jun. 6, 2011, 2 pages.
International Preliminary Report on Patentability received for PCT Patent Application No. PCT/US2011/041462, dated Jan. 9, 2014, 10 pages.
International Preliminary Report on Patentability received for PCT Patent Application No. PCT/US2013/073508, dated Jun. 16, 2016, 13 pages.
International Search Report and Written Opinion received for PCT Patent Application No. PCT/US2011/041462, dated Feb. 27, 2012, 15 pages.
International Search Report and Written Opinion received for PCT Patent Application No. PCT/US2013/073508, dated Mar. 4, 2014, 14 pages.
Non Final Office Action received for U.S. Appl. No. 15/171,947, dated Feb. 19, 2019, 9 pages.
Office Action received for European Application No. 11868058.6, dated May 17, 2017, 4 pages.
Omnifit Solvent Safety Bottle Caps, Bio Chern Fluidics, known at least as early as Jun. 6, 2011, 16 pages.
PTFE Faced Silicone Septa for GL25 Open Top PBT Screw Cap, Corning Life Sciences Catalog, https://catalog2.corning.com/LifeSciences/en-US/Shopping/ProductDetails.a-spx?category . . . , known at least as early as Mar. 18, 2014, 1 page.
Sanl-Tech EZ Top Container Closure, Saint-Gobain Performance Plastics, known at least as early as Jun. 6, 2011, 2 pages.
International Search Report and the Written Opinion of the International Searching Authority for PCT/US2018/060828 dated Feb. 1, 2019, 11 pages.
International Search Report and the Written Opinion of the International Searching Authority for PCT/US2019/061229 dated Jan. 29, 2020, 9 pages.
International Preliminary Report on Patentability received for PCT Patent Application No. PCT/US2019/061229, dated May 27, 2021, 9 pages.
International Preliminary Report on Patentability received for PCT Patent Application No. PCT/US2018/060828, dated May 28, 2020, 10 pages.
Screenshots of Lucky Penny Shop video; publicly available video, published Aug. 5, 2014, titled "Bunch O Balloons Review 100 water balloons in less than a minute!—Water Balloon Fight!", web address: https://www.youtube.com/wtch?v=S1 DaXYT602A (Year: 2014), 4 pages.
PCT/US2011/041462, Jun. 22, 2011, Vessel Closures and Methods for Using and Manufacturing Same, 37 pages.

\* cited by examiner

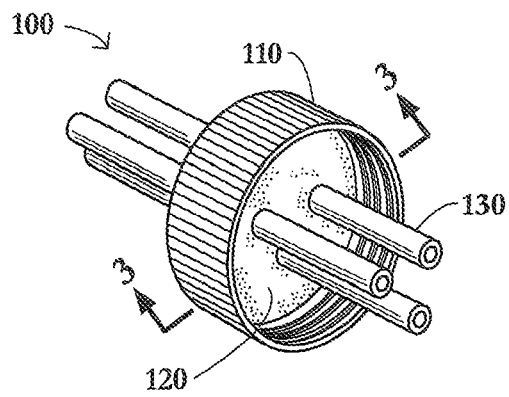
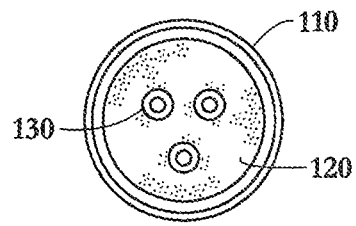
FIG. 1  FIG. 2
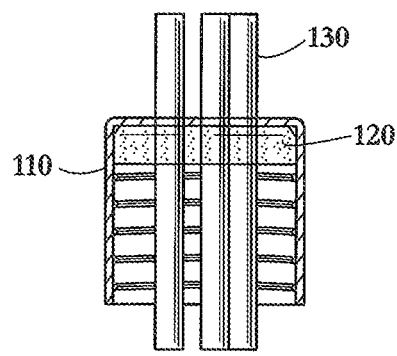
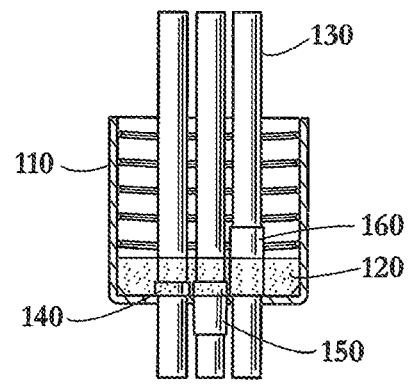
FIG. 3  FIG. 4
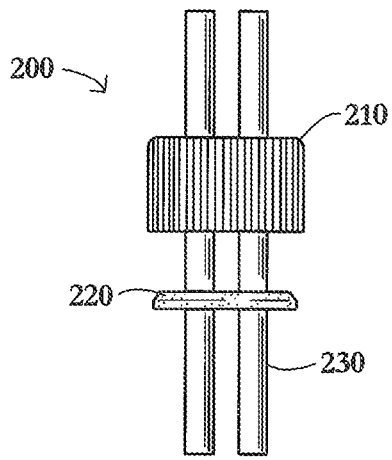
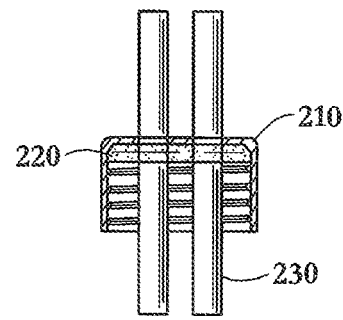
FIG. 5  FIG. 6

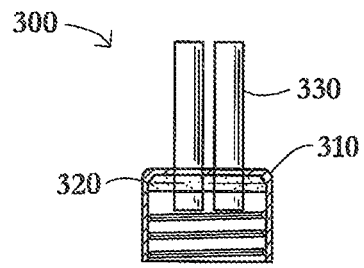
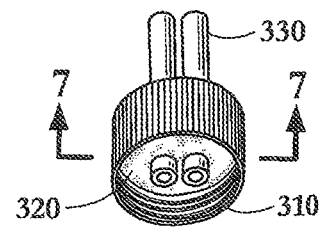
FIG. 7  FIG. 8
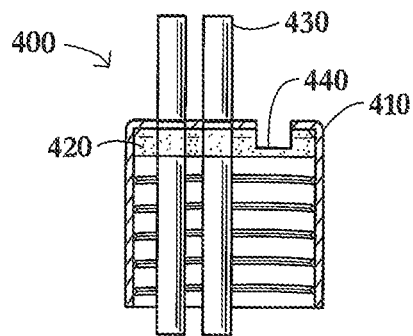
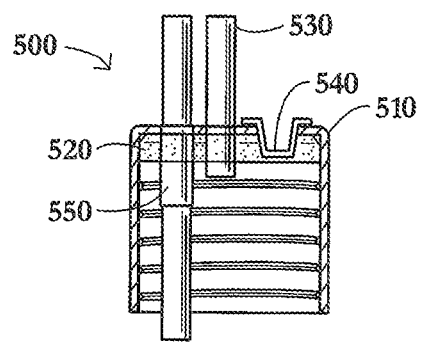
FIG. 9  FIG. 10
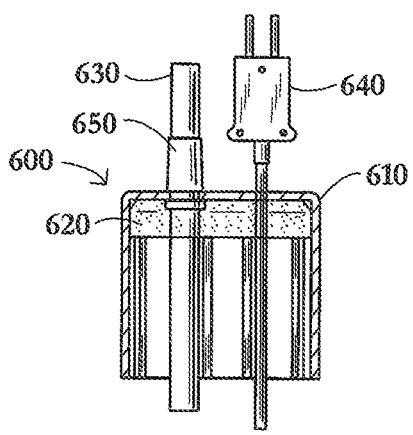
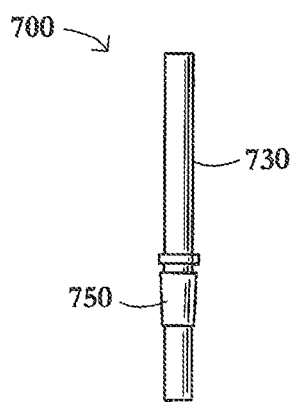
FIG. 11  FIG. 12

VESSEL CLOSURES AND METHODS FOR USING AND MANUFACTURING SAME

PRIORITY

The present application is a continuation of U.S. patent application Ser. No. 16/015,256, filed Jun. 22, 2018, which is a continuation-in-part of U.S. patent application Ser. No. 14/128,259, filed Mar. 19, 2014, now 10,006,567, which is a National Stage Entry of PCT/US2011/041462, filed Jun. 22, 2011. The entire contents of each of these disclosures are hereby incorporated by reference.

TECHNICAL FIELD

This disclosure relates generally to vessel closures and more specifically to vessel closures having inserts, such as tubing, extending through the vessel closure.

BACKGROUND

During certain manufacturing processes, vessels containing various fluids are used. Often it is necessary to transfer fluid into or out of a vessel during the process and do so in a substantially aseptic manner without breaching the closed nature of the system. In particular, the need to transfer fluid often arises in the manufacturing and processing of pharmaceuticals, biopharmaceuticals, or other biotechnology applications where processes are conducted in vessels of varying shapes and sizes. The need for fluid transfer into and out of a vessel arises in other applications and industries as well, including but not limited to the production of food, cosmetics, paint, chemicals, including hazardous chemicals, and the transfer and handling of semiconductor fluids.

Regardless of the industry, during transfers or sampling, the fluid in a vessel must remain substantially free of contaminants. In addition, when making such transfers, it is desirable to keep the environment surrounding a vessel free from contamination by the contents of the vessel or a sample taken therefrom. It is often the case that, throughout the manufacturing process, there is a need to maintain fluid communication with the interior of the vessel by way of, for example, tubing extending through a vessel closure from the exterior of the vessel into the interior of the vessel. To accomplish a substantially aseptic transfer, it is desirable to control the environment through which the fluid flows, for example, the pathway from a vessel to a sample container should be substantially aseptic along the entire pathway. Furthermore, it is desirable that the vessel closure be safe for use, reliable, and of low-cost construction.

It is also desirable to transfer fluid using a vessel closure which is pre-sterilized and disposable. A pre-sterilized, disposable vessel closure avoids the need for an operator to sterilize the vessel closure for use. Further, such sterilization can damage vessel closures and render them useless before their first use.

Known vessel closures utilize either thermoplastic or elastomeric tubing to create fluid communication with the interior of a vessel. Known vessel closures use, for example, all elastomeric tubing, such as silicone tubing, or utilize all thermoplastic tubing, such as C-Flex® tubing. Vessel closures incorporating elastomeric tubing are often manufactured using insert injection molding at temperatures between 350° to 400° F. These temperatures will melt or damage thermoplastic tubing. Further, vessel closures manufactured with silicone seals have not heretofore included thermoplastic tubing due to the lack of adhesion of silicone directly onto thermoplastic tubing.

Thus, what is needed is a vessel closure with a seal capable of adhering to silicone tubing or other inserts. What is also needed is a vessel closure with a seal with both elastomeric and thermoplastic tubing within the same vessel closure wherein the tubing creates a substantially aseptic fluid pathway into and out of a vessel. What is further needed are manufacturing techniques for manufacturing a low cost, disposable vessel closure with both elastomeric and thermoplastic tubing wherein the tubing creates a substantially aseptic fluid pathway into and out of a vessel. What is also needed is a method of using the aforementioned vessel closures to circulate fluid into and out of a vessel while also having the option of controlling the temperature of the fluid.

SUMMARY

Briefly described, a vessel closure comprising a body, one or more apertures extending axially through the body, one or more inserts extending axially through one or more apertures, and a cast seal disposed within the body and surrounding each insert. In one embodiment, the vessel closure may have one or more inserts comprising silicone tubing. In one embodiment, the cast seal is pourable, self-leveling silicone, such as room temperature vulcanizing ("RTV") silicone.

In one embodiment, a gasket is disposed between a pair of vessel closures, which are held together by a clamp, to form a fluid transfer hub. The fluid transfer hub can create a manifold where fluid from a source is distributed to a plurality of vessels.

In another embodiment, briefly described, a tubing assembly in a vessel closure comprising one or more thermoplastic tubes extending axially through one or more apertures extending through the vessel closure; an anchor adhesively attached to a portion of each thermoplastic tube, the anchor capable of bonding with a casting agent; and a casting agent securing each anchor and thermoplastic tube through each aperture. The thermoplastic tubes may be C-Flex® tubing.

In another embodiment, briefly described, a tubing assembly in a vessel closure comprising flexible tubing extending through an aperture in the closure; a deformable sleeve adhesively attached to and surrounding at least a portion of the flexible tubing; the sleeve being formed of a material having plasticity such that pressure applied to the sleeve causes the sleeve to deform about and seal the flexible tubing and upon continued application of pressure to the sleeve, the sleeve and flexible tubing are cut and the sleeve retains a deformed shape substantially sealing the tubing; and a cast seal surrounding the sleeve.

In a further embodiment, briefly described, a vessel closure comprising a body, at least two apertures through the body, and flexible tubing passing through the at least two apertures wherein the ends of the tubing are both directed into the interior of the vessel thereby forming a loop on the exterior of the vessel.

Also, briefly described, a method of manufacturing a vessel closure comprising a body, one or more apertures extending axially through the body, and an insert extending axially through one or more apertures. The method comprising creating one or more apertures in a body; inserting an insert axially through one or more apertures; casting a casting agent into the body; and curing the casting agent to form a seal around and bond to the one or more inserts.

In another embodiment, briefly described, a method of manufacturing a vessel closure, the vessel closure comprising one or more apertures through a body with tubing extending through the one or more apertures; the method comprising creating one or more apertures in a body; inserting silicone tubing through at least one aperture; inserting thermoplastic tubing through at least one other aperture wherein at least a portion of the thermoplastic tubing is surrounded by a sleeve adhesively attached to the tubing, wherein the outer surface of the sleeve is capable of bonding with a casting agent; casting a casting agent into the body; and curing the casting agent to form a seal around and bond to the silicone tubing and to the at least one sleeve surrounding the thermoplastic tubing. In one embodiment, the thermoplastic tubing may be C-Flex® tubing.

Also, briefly described, a method of circulating a fluid into and out of a vessel comprising sealing a vessel with a closure, the closure comprising a body, at least two apertures through the body, and flexible tubing routed through the at least two apertures so the ends of the tubing are both directed into the interior of the vessel thereby forming a loop on the exterior of the vessel; attaching circulating means to the loop on the exterior of the vessel and using circulating means to circulate fluid out of and into the vessel through the flexible tubing. In one embodiment, the fluid is circulated using a peristaltic pump.

Thus, vessel closures, methods of manufacturing the same, and methods of utilizing the same are disclosed that possess distinct attributes and represent distinct improvements over the prior art. These and other aspects, features, and advantages of the vessel closures of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

BRIEF DESCRIPTION OF THE DRAWINGS

FIG. 1 is a perspective view of a vessel closure, cast seal, and three tubes.

FIG. 2 is a bottom view of a vessel closure, cast seal, and three tubes.

FIG. 3 is a cross section of a vessel closure, cast seal, and three tubes.

FIG. 4 is a cross section of a vessel closure, cast seal, three tubes, and three different anchors, illustrating a variety of anchors that may be used.

FIG. 5 is a side view of a vessel closure, cast seal, and two tubes, illustrating the seal pulled away from the interior of the vessel closure.

FIG. 6 is a cross-section of a vessel closure, cast seal, and two tubes, illustrating the invention in a relatively smaller vessel closure than shown in FIG. 1.

FIG. 7 is a cross-section of a vessel closure, cast seal, two tubes, illustrated in yet a different relatively smaller vessel closure.

FIG. 8 is a perspective view of a vessel closure, cast seal, and two tubes.

FIG. 9 is a cross-section of a vessel closure, cast seal, two tubes, and an aperture in the vessel closure sealed only by the cast seal, illustrating a pierceable section of the seal.

FIG. 10 is a cross-section of a vessel closure, cast seal, two tubes, and a puncture site, illustrating an embodiment with an anchor attached to one tube, a tube with no anchor, and a specialized puncture site over one aperture in the vessel closure.

FIG. 11 is a cross-section of a vessel closure depicting a temperature probe, tube, and anchor.

FIG. 12 is a side view of a tube and anchor.

DETAILED DESCRIPTION OF EXEMPLARY EMBODIMENTS

Figure 13:
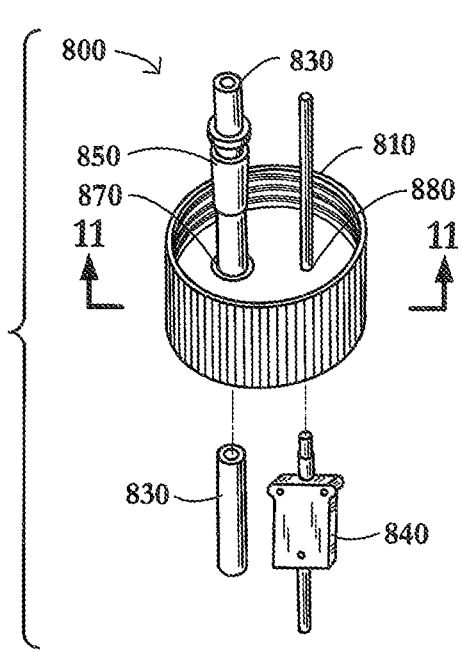
FIG. 13 is a perspective view of a vessel closure, temperature probe, tube, and anchor before the tube and anchor are connected to the vessel closure and before a seal is cast around the anchor, tube, and probe.

Certain exemplary embodiments of the present invention are described below and illustrated in the accompanying figures. The embodiments described are only for purposes of illustrating the present invention and should not be interpreted as limiting the scope of the invention, which of course, is limited only by the claims below. Other embodiments of the invention, and certain modifications and improvements of the described embodiments, will occur to those skilled in the art, and all such alternate embodiments, modifications, and improvements are within the scope of the present invention.

Referring now in more detail to the drawing figures, wherein like reference numerals indicate like parts throughout the several views, FIG. 1 depicts a first exemplary vessel closure, in this case a vessel closure with multiple tubes extending through the vessel closure thereby creating fluid communication between the interior and exterior of a vessel onto which the vessel closure may be placed. It should be understood that the vessel closure is not limited to use with any particular fluids but, depending on the size and composition of the inserts, may be used with fluids with particulates or having a high viscosity or with fluids having no or very little particulate content or low viscosity.

The vessel closure 100 illustrated in FIG. 1 generally depicts a body, inserts, and a seal shown assembled together to form a single vessel closure. The vessel closure 100 has a body 110, discussed in more detail below, one or more apertures extending axially through the body, inserts 130 extending axially through each aperture, and a cast seal 120 disposed within the body and surrounding each insert. The vessel closure is not limited to this number of inserts, but may incorporate more or fewer inserts. The vessel closure is suitable for use with vessels that include without limitation: containers, beakers, bottles, canisters, flasks, bags, receptacles, tanks, vats, vials, tubes, and the like that are generally used to contain fluids, slurries, and other similar substances.

In the vessel closure illustrated in FIG. 1, the body is a cap. Suitable caps for the vessel closure include those commonly used in the field of pharmaceutical, biopharmaceutical, and biotechnology processing. Such caps include: a 38-430 cap with an outer diameter at the open end of approximately 42 mm and being approximately 29 mm tall (as depicted in FIGS. 1, 4, 9, 10, and 17-19); a centrifuge cap having an outer diameter at the open end of approximately 34 mm and being approximately 13 mm tall (such as depicted in FIGS. 5 and 6); a 20-415 cap with an outer diameter at the open end of approximately 24 mm and being approximately 14.6 mm tall (such as depicted in FIGS. 7 and 8); and a GL-45 cap having an outer diameter at the open end of approximately 53.7 mm and being approximately 25.5 mm tall. The invention, however, is not limited to a cap of any particular dimensions. Bodies of vessel closures may be made from thermoplastics such as polyolefins, polypropylene, polyethylene, polysulfone, polyester, polycarbonate, and glass filled thermoplastics. The invention, however, is not limited to a cap made from any particular material(s). The bodies may also be made from thermosets such as epoxies, pheonolics, and novolacs. The body may also be a hygienic or sanitary clamp having dimensions disclosed in ASME BPE table DT-5-2 ("Hygienic Clamp Ferrule Standard Dimensions and Tolerances") (2009), which is incorporated by reference herein in its entirety. The body is not limited to caps or hygienic clamps but may constitute any suitable closure that seals the interior of a vessel from the exterior environment.

FIG. 1 further depicts three inserts 130 extending axially through the body. The inserts extend through apertures in the body. The number of apertures in the body may correspond with the number of inserts to be placed in the body.

Also depicted in FIG. 1 is a cast seal 120. In a preferred embodiment the cast seal is constructed from a self-leveling, pourable silicone such as room temperature vulcanizing ("RTV") silicone. The RTV silicone may be a two-component system (base plus curative) ranging in hardness from relatively soft to a medium hardness, such as from approximately 9 Shore A to approximately 56 Shore A. Suitable RTV silicones include Wacker® Elastocil® RT 622, a pourable, addition-cured two-component silicone rubber that vulcanizes at room temperature; and Blue Star Silicones Rhodorsil® RTV 1556, a two-component, high strength, addition-cured, room temperature or heat vulcanized silicone rubber compound. Both the Wacker® Elastocil® RT 622 and the Bluestar Silicones Rhodorsil® RTV 1556 have a viscosity of approximately 12,000 cP (mPa·s). The aforementioned silicones and their equivalents offer low viscosity, high tear cut resistance, high temperature and chemical resistance, excellent flexibility, low shrinkage, and the ability to cure a cast silicone seal at temperatures as low as approximately 24° C. (75° F.). In another embodiment, the casting agent is a perfluoropolyether liquid. A preferred perfluoropolyether liquid is Sifel 2167, available from Shin-Etsu Chemical Co., Ltd.

In an embodiment, the cast seal is disposed within the body of the vessel closure so that when the body is attached to a vessel opening, such as a bottle opening, the cast seal creates a seal between the interior of the vessel and the exterior environment. Preferably, the seal formed by the vessel closure between the interior of the vessel and the exterior environment is substantially aseptic. As best shown in FIGS. 1 and 3, the cast seal 120 surrounds the inserts 130, thereby creating a unified seal and insert subassembly. In an embodiment, the seal between the cast seal 120 and insert 130 is substantially aseptic.

In one embodiment, the inserts are silicone tubing. For clarity, only a portion of the silicone tubing is shown in FIG. 1. The tubing may be of any length suitable and necessary for the desired process. In an embodiment, at least a portion of the silicone tubing is treated with a primer where the cast silicone surrounds the tubing. Suitable primers are SS-4155 available from Momentive™, Med-162 available from NuSil Technology, and Rodorsil® V-O6C available from Bluestar Silicones.

Referring now to FIG. 2, a bottom-view of a vessel closure shows the body 110, the inserts 130, and the cast seal 120 partially filling the body of the vessel closure and surrounding the exterior of the inserts extending through the apertures in the body. As shown in FIG. 3, which is a cross-section of the vessel closure, the body 110 contains the cast seal 120 and the inserts extend axially through the body 110 and the cast seal 120.

Turning now to FIG. 4, a vessel closure is shown with a variety of anchors 140, 150, and 160. For clarity, the selection and depiction of various anchors is for illustrative purposes only. The vessel closures may have any variety of different anchors, have all the same anchors, or no anchors at all. Specifically, FIG. 4 depicts three different anchors 140, 150, and 160, a body 110, a cast seal 120, and three inserts 130, in this case, tubing. Anchor 140 is a retaining nut affixed in place around the silicone tube insert 130. The retaining nut prevents the insert from being pulled out of a vessel. Anchor 150 has a retaining nut portion and a cone-shaped portion. (Anchor 150 is also shown as anchor 750 in FIG. 12.) The retaining nut portion is located on the interior of the body, while the cone-shaped section is on the exterior of the body. Anchor 150 prevents the insert from being pulled out of a vessel or being pulled into a vessel when, for example, a vacuum is placed on the interior of the vessel. Anchor 160 is a sleeve, also referred to herein as an anchor sleeve, that prevents the insert from being pulled out of the body. Anchor sleeve 160 also provides a surface to which the cast seal may bond. The cast seal may also bond to an anchor and the insert on which the anchor is placed. Regardless of the shape of the anchor, the cast seal 120 bonds to the anchor. The anchors may be constructed of such material that is particularly suitable for bonding with the cast seal, such as metal (aluminum, stainless steel, etc.), plastic, glass-filled plastic, ceramics, and composites. In an embodiment, the anchors are adhesively attached to the inserts. Thus, when an embodiment of a vessel closure is constructed, the anchor is adhesively attached to the insert, for example, a tube; the cast seal is bonded to the anchor, and the anchor secures the one or more tubes and cast seal to the body of the vessel closure.

Figure 20:
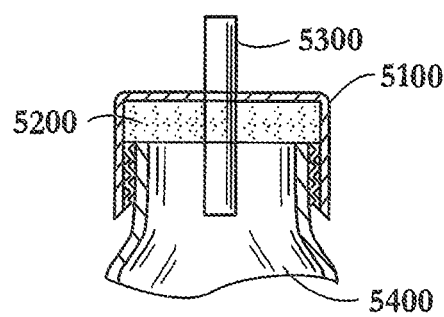
FIG. 20 is a cross-section of a vessel, vessel closure, seal, and silicone tube, illustrating the vessel closure sealed to the vessel.

In another embodiment, the cast seal 120 is attached to the body by way of priming at least a portion of the body and adhesively attaching the cast seal to the body. In this embodiment, the cast seal will not pull away from the interior of the body. However, in other embodiments the cast seal need not necessarily be attached to the body. As best shown in FIG. 5, a vessel closure 200 may have a body 210, apertures extending axially through the body (not shown in FIG. 5), a cast seal 220, and two inserts 230, in this case, silicone tubing. The body shown in FIG. 5 represents a centrifuge cap. In FIG. 5, the cast seal 220 is shown pulled away from the body 210. Upon placement of the body of the vessel closure to a vessel, for example, placing a cap on a bottle, the cast seal 220 will be seated within the body. FIG. 20 shows such an arrangement and is discussed in detail below. FIG. 6 shows the cast insert seated within the body 210 without the presence of a vessel. As with the vessel closure shown in FIG. 1, the vessel closure in FIG. 4 shows two inserts but any number of inserts could be used.

Returning to FIG. 4, the vessel closure may have only inserts such as the insert with anchor sleeve 160. In an embodiment, the anchor sleeve 160 adhesively attaches to the insert. In one embodiment, the insert is thermoplastic tubing, such as C-Flex® tubing. When anchor sleeves partially or completely surround each insert, the seal need not be constructed of cast silicone but may be made of any casting agent capable of bonding to the anchor sleeve. For example, in applications involving solvents, a casting agent such as liquid perfluoropolyether could be used. Regardless of which casting agent is used, the casting agent is preferably aseptically sealed to the anchor.

In an embodiment, at least a portion of the anchors are treated with a primer where the anchor sleeve contacts the casting agent. In yet another embodiment, the vessel closure may contain inserts comprising elastomeric tubing wherein at least a portion of the tubing is surrounded by an anchor sleeve and silicone tubing extends through the body and seal. In such embodiment, the silicone tubing is not surrounded, either partially or wholly by an anchor sleeve. In this embodiment, the preferred casting agent is liquid silicone.

Again returning to FIG. 4, anchor sleeve 160 may be a deformable sleeve, such as those disclosed in PCT/US08/0488, which is incorporated by reference herein in its entirety and owned by the assignee of the instant application. In an embodiment, the deformable sleeve surrounds and is adhesively attached to flexible tubing. In one embodiment, the deformable sleeve is attached to the flexible tubing at a location that facilitates substantially sealing, cutting, and detaching the deformable sleeve. In such embodiments, the sleeved is formed of a material having plasticity such that pressure applied to the sleeve causes the sleeve to deform about and seal the flexible tubing and upon continued application of pressure to the sleeve, the sleeve and flexible tubing are cut and the sleeve retains a deformed shape, thereby substantially sealing the tubing. In these embodiments, the flexible tubing is thermoplastic tubing, elastomeric tubing, or a combination of thermoplastic and elastomeric tubing. Further, when a deformable sleeve is used, the casting agent may adhere to and aseptically seal with the deformable sleeve.

Turning now to FIGS. 7 and 8, a vessel closure 300 is shown representing a body 310 representative of a 20-415 cap, a cast seal 320, and two inserts 330. The inserts may be silicone tubing.

FIG. 9 illustrates an embodiment of a vessel closure 400 having a body 410, a cast seal 420, inserts 430, and a pierceable recess 440 formed in the cast seal 420. The pierceable recess 440 is a section of the cast seal 420 in which a removable insert was set during the casting and curing of the silicone and later removed to form an area of the cast seal 420 that is thinner than the remainder of the cast seal. In one embodiment the pierceable recess 440 is thin enough for a hypodermic needle to be inserted through the pierceable recess 440 thereby accessing the interior of a vessel so that fluid may be introduced into or removed from a vessel.

FIG. 10 illustrates another embodiment of a vessel closure 500 having a body 510, a cast seal 520, inserts 530, and a pierceable insert 540. The pierceable insert 540 may be constructed from silicone or other suitable material that would allow a hypodermic or other similar needle to pierce the insert and thereby introduce or remove fluid from a vessel. Also shown in in FIG. 10 is an anchor sleeve 550. FIG. 10 illustrates an example of a vessel closure potentially having three different inserts. The tubing without the sleeve may be silicone while the tubing with the sleeve could be elastomeric tubing, such as C-Flex® tubing. Lastly, the pierceable insert 540 represents the third type of insert.

FIG. 11 depicts yet another embodiment of a vessel closure 600 having a body 610, a cast insert 620, inserts 630 and 640, and an anchor 650. Insert 630 may be, for example, silicone tubing, and the anchor 650 is constructed with a retaining nut portion in the interior of the body 610 and a conical section on the exterior of the body 610, thereby securing the insert 630 to body 610 by way of, for example, a friction fit. Insert 640 is a temperature probe. Various inserts may be used in the vessel closures including but not limited to: tubing (including but not limited to elastomeric and thermoplastic tubing), temperature probes, pH sensors, pierceable inserts, strain relief boots, dip tubes, barbed fittings, luers, and quick connect fittings. The invention is not limited to the aforementioned inserts. Inserts of any size, function, and construction may be used.

Further, check valves may be attached to tubing extending into the interior of a vessel. Use of such check valves keeps fluids from entering a vessel until a requisite and sufficient force is applied to the fluid to open the check valve. Such force could be applied, for example, by a syringe or pump. In one embodiment, check valves such as Model #110 from Smart Products may be used.

FIG. 12 illustrates an insert 700 comprised of tubing 730 and an anchor 750. The anchor 750 is the same anchor as depicted in FIG. 11 and illustrates a how the anchor may be friction fit into an aperture in the body 610 by pressing the conical section into and through an aperture until the anchor snaps into place.

As shown best in FIG. 13, various inserts extend axially through apertures in the body during the manufacturing process before a casting agent is poured into the body of a vessel closure to form a seal. Specifically, FIG. 13 illustrates a perspective view of a vessel closure 800, a body 810, an insert 830, a temperature probe 840, an anchor sleeve 850, and apertures 870 and 880 in the body. As shown in FIG. 13, the insert 830 and anchor sleeve 850 combination have not yet been fully inserted into aperture 870 in the body. In addition, the cast seal (not shown) has not yet been poured.

Figure 14:
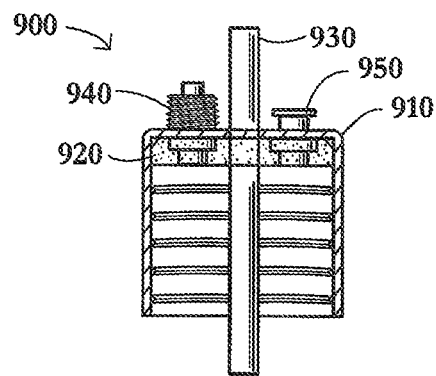
FIG. 14 is a cross-section of a vessel closure, two fittings, and a tube wherein the fittings shown are a male and female luer.

FIG. 14 illustrates a vessel closure 900, a body 910, a cast seal 920, and three inserts 930, 940, and 950. In a preferred embodiment insert 930 is silicone tubing. Insert 940 is a male luer fitting and insert 950 is a female luer fitting.

Figure 15:
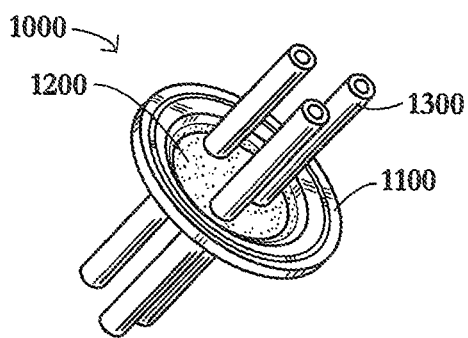
FIG. 15 is a perspective view of a tri-clamp closure, three tubes, and a cast seal.
Figure 16:
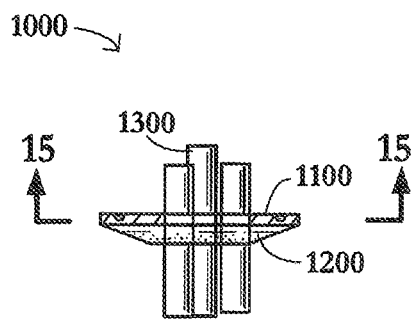
FIG. 16 is a cross-section of a tri-clamp closure, three tubes, and a cast seal.

FIG. 15 depicts a tri-clamp vessel closure 1000 comprising a body 1100, a cast seal 1200, and inserts 1300. FIG. 16 shows a cross-section of the tri-clamp vessel closure 1000 comprising a body 1100, a cast seal 1200, and inserts 1300. Tri-clamp closures may be made with inserts other than the tubing inserts shown in FIGS. 15 and 16. Tubing is shown as merely an example of the type of insert that may be used.

Figure 17:
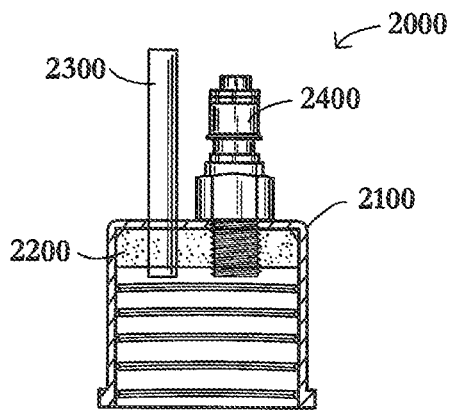
FIG. 17 is a cross-section of a closure, a tube, and fitting wherein the fitting shown is a quick connect fitting.

FIG. 17 illustrates a vessel closure 2000, a body 2100, a cast seal 2200, and two inserts 2300 and 2400. In an embodiment insert 2300 is a silicone tube. Insert 2400 depicts a male quick connect fitting. A quick connect fitting may be further secured to the body of the vessel closure by affixing a nut to the threaded portion of the insert that extends into the interior of the body. The body 2100 represents a 38-430 cap.

Figure 18:
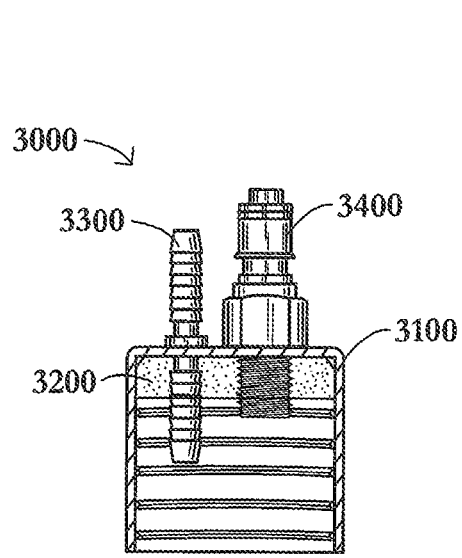
FIG. 18 is a side view of a closure and two fittings wherein the fittings are a barbed fitting and a quick connect fitting.

FIG. 18 depicts a vessel closure 3000, a body 3100, a cast seal 3200, and two inserts 3300 and 3400. Insert 3300 is a barbed fitting of the type that accepts flexible tubing, such as silicone or thermoplastic tubing. Insert 3400 is a male quick connect fitting. In an embodiment, the barbed insert may have a barbed extension extending into the interior of the body as well as extending away from the exterior of the body so that tubes may be attached extending into and out of a vessel.

Figure 19:
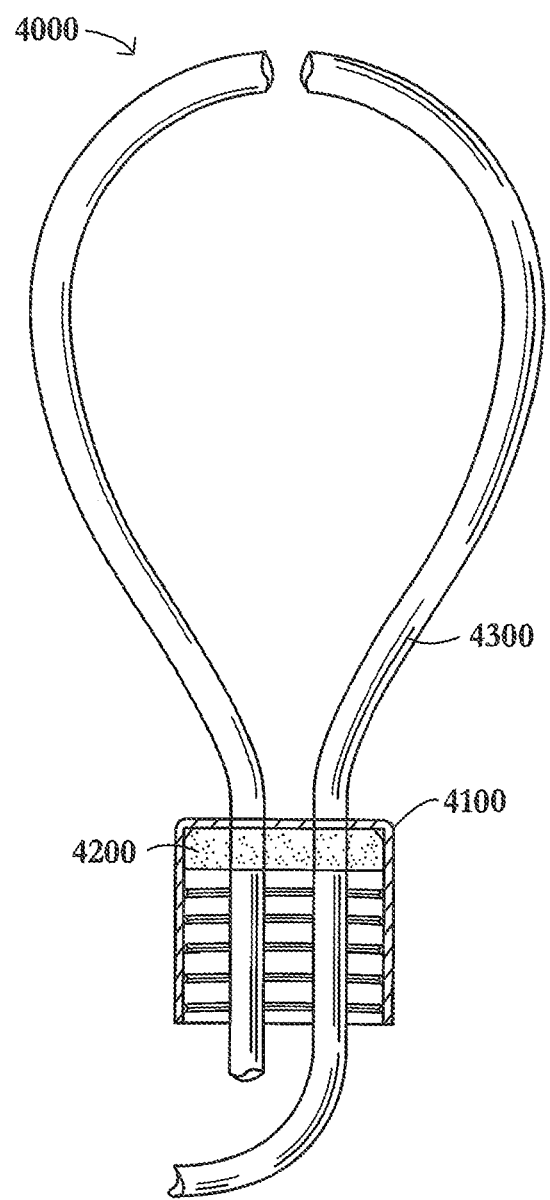
FIG. 19 is a cross-section of a vessel closure and tubing, illustrating the tubing routed through the closure to form a loop on the exterior of the closure.

FIG. 19 depicts a vessel closure 4000, a body 4100, a cast seal 4200, and tubing 4300. Body 4100 has at least two apertures so that tubing 4300 passes through each aperture and the ends of the tubing are both directed into the interior of a vessel thereby forming a loop on the exterior of the vessel. The loop show in FIG. 19 is for illustrative purposes only and the loop on the inventive vessel closure may made in any length necessary to accommodate pumping or pumping and temperature control. The vessel closure illustrated in FIG. 19 may be used to circulate fluid into and out of a vessel without exposure to the environment outside of the vessel, thereby forming a closed system utilizing few components. In an embodiment, a peristaltic pump is connected to the loop of tubing outside the vessel and used to circulate the fluid. In yet another embodiment, a heat exchanger is used, instead of or in addition to a pump, to regulate the temperature of the fluid.

As best shown in FIG. 20, the cast seals disclosed herein may be sealingly compressed between the body of a vessel closure and a vessel by tightening the closure onto a vessel. FIG. 20 depicts a vessel closure body 5100 mechanically depressed to a vessel by the body being tightened to a vessel 5400 thereby compressing the cast seal 5200 against the vessel. In a preferred embodiment, the cast seal is aseptically sealed to the vessel.

Figure 21:
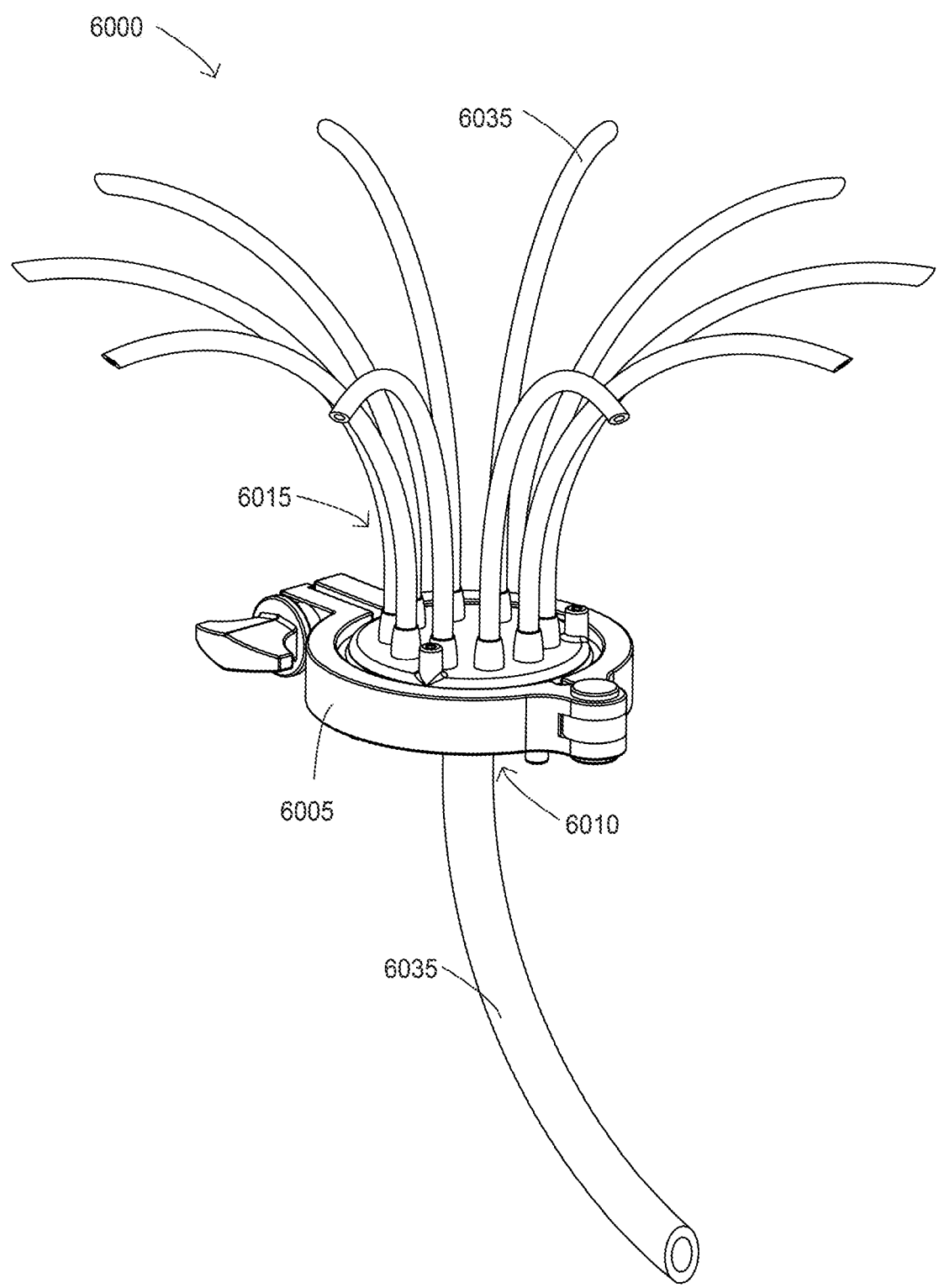
FIG. 21 is a perspective view of a fluid transfer hub formed from a pair of vessel closures.
Figure 22:
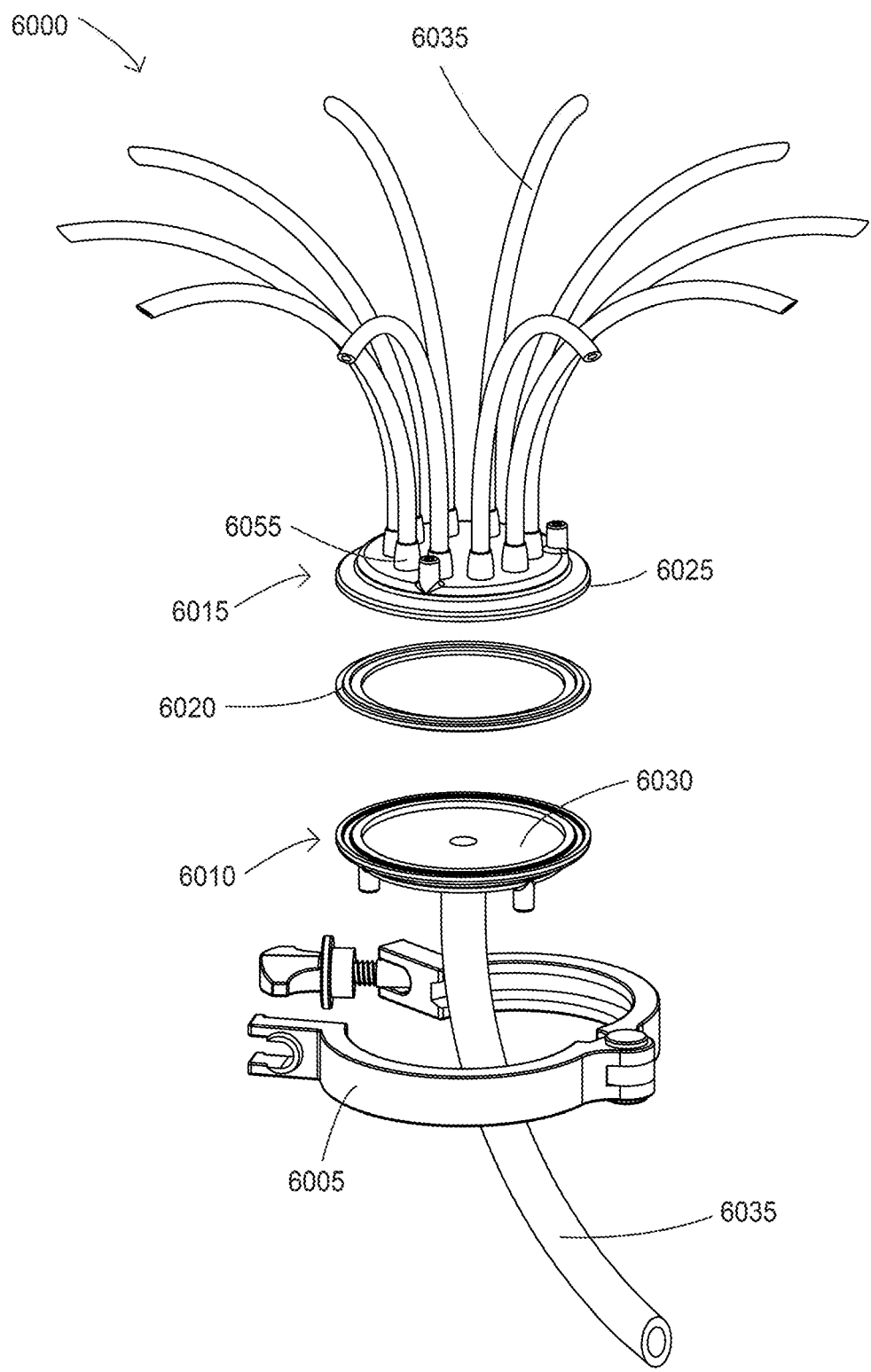
FIG. 22 is an exploded view of the fluid transfer hub.

The vessel closures discussed above, particularly the tri-clamp vessel closures 1000 (FIG. 15) may be combined to create additional, alternative embodiments. FIG. 21 depicts a fluid transfer hub 6000. FIG. 22 depicts an exploded view of the fluid transfer hub 6000 to provide a more clear illustration of the components thereof according to one embodiment. The fluid transfer hub 6000 may be comprised of a tri-clamp 6005, a first tri-clamp vessel closure 6010, a second tri-clamp vessel closure 6015, and a gasket 6020.

The tri-clamp 6005 in the illustrated embodiment is a 2-segment, single-hinge type clamp. Alternatives that are well-known to one having ordinary skill in the art include 3-segment, double-hinge clamps, and high-pressure, no-hinge type clamps. Each tri-clamp vessel closure 6010, 6015 is a tri-clamp fitting that includes a body 6025, a cast seal 6030, and at least one insert 6035. The body 6025 may be substantially similar to the body 1100 of the tri-clamp vessel closure 1000 (FIG. 15). The body 6025 may include one or more apertures extending axially through the body. The body 6025 is a clamp body and can have any dimensions, but may be preferably among the standard clamp dimensions for hygienic and sanitary uses as discussed above. Further, the body 6025 may be formed from any of the suitable body materials discussed above. Similarly, the cast seal 6030 of the vessel closures 6010, 6015 of the fluid transfer hub 6000 may be formed from the same suitable materials, and formed using the same methods, as discussed above with respect to the cast seal 120 (FIGS. 1-4). Further, the inserts 6035 may be silicone tubing, thermoplastic tubing, or other components consistent with the inserts discussed elsewhere in the present disclosure.

To help create a seal between the two tri-clamp vessel closures 6010, 6015, a gasket 6020 is provided. Gaskets 6020 are available in standard sizes that corresponding with the standard dimensions of tri-clamps and their corresponding fittings. Gaskets 6020 are available in several materials, including copolymers of acrylonitrile and butadiene (BUNA-N), VITON®, fluoroelastomers as defined by ASTM D1418 (FKM), ethylene propylene diene monomer (EPDM), polytetrafluoroethylene (PTFE), silicone, and others. An open gasket 6020 is illustrated in FIG. 22, but other types of gaskets are available that may be used within the fluid transfer hub 6000. Alternative gaskets 6020 include orifice gaskets, screen gaskets, and perforated plate gaskets that may control flow of a fluid through the fluid transfer hub 6000, or provide a filtering function. Each of these alternative gaskets are available in several sizes, or can be customized, based upon the dimensions of the fittings, the orifice diameter through the gasket, or the pore size of the perforated plate or screen gaskets. Suitable gaskets 6020 are available from Flow Smart Inc. and others.

Figure 23:
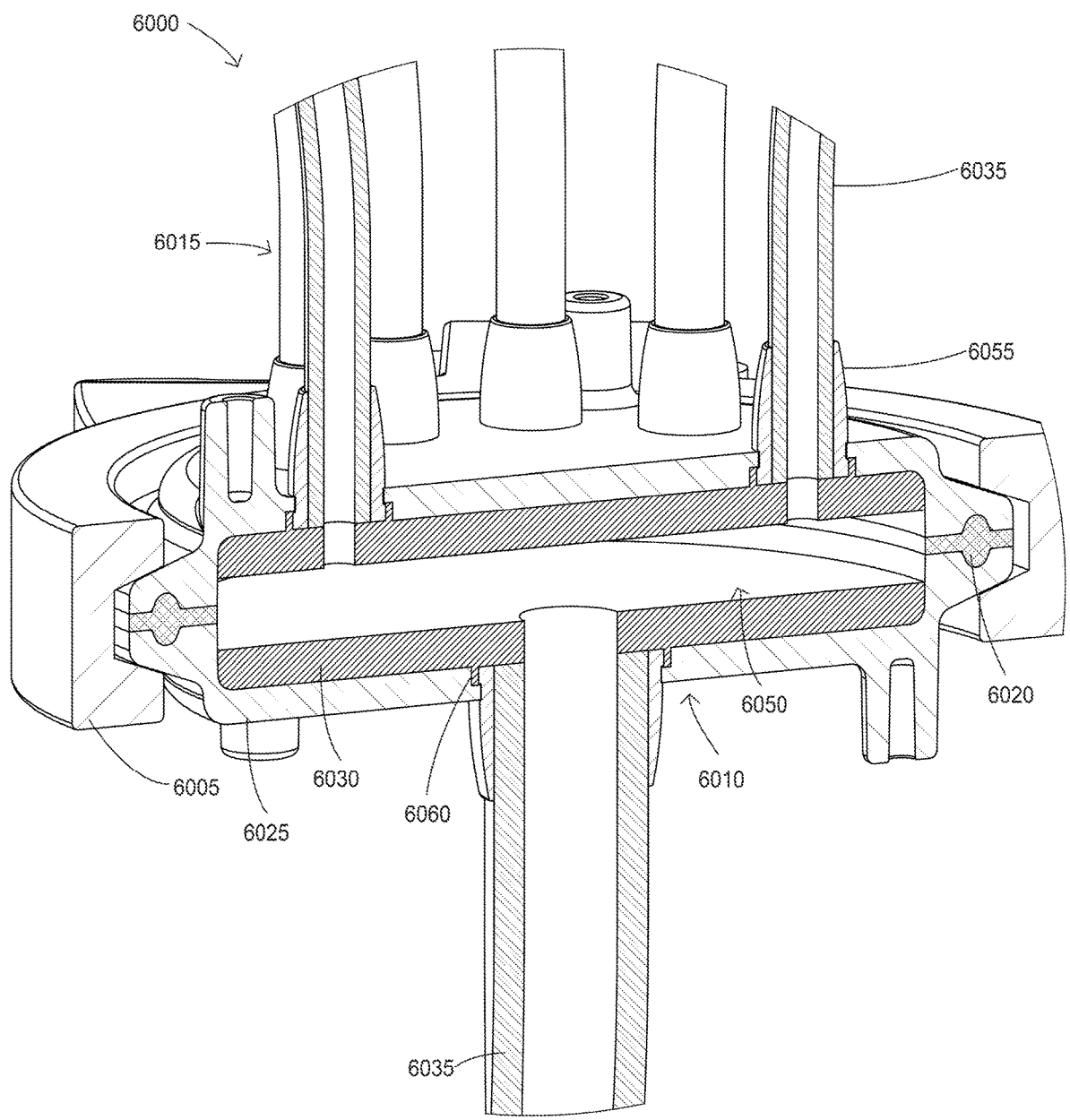
FIG. 23 is a cross-section of the fluid transfer hub according to a first embodiment.
Figure 24:
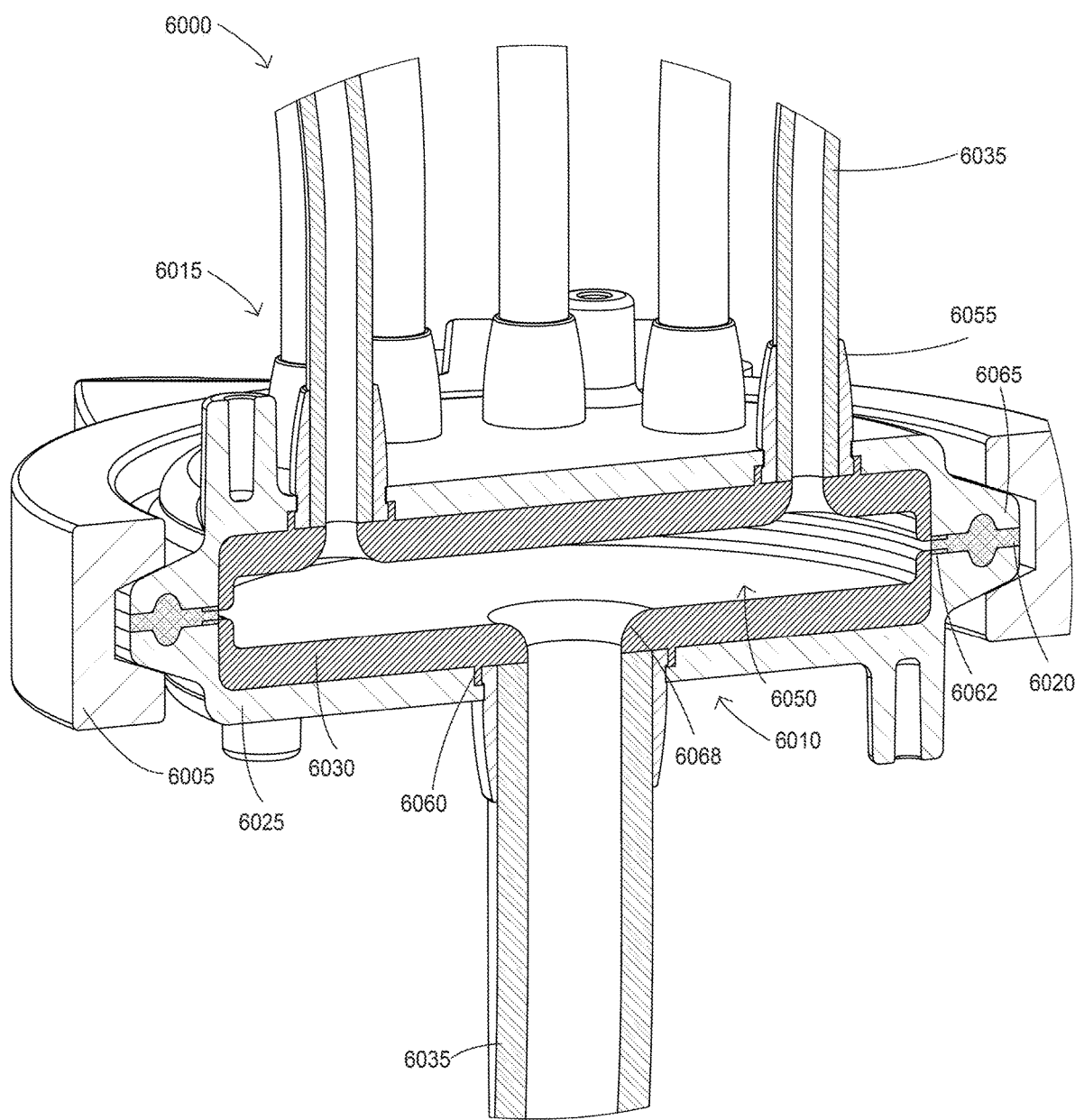
FIG. 24 is a cross-section of the fluid transfer hub according to a second embodiment.

FIGS. 23 and 24 illustrate alternative cross sections of a fluid transfer hub 6000. The tri-clamp 6005, first tri-clamp vessel closure 6010, and second tri-clamp vessel closure 6015 are illustrated along with the gasket 6020. The inserts 6035 of each tri-clamp vessel closure 6010, 6015 include tubing. In the illustrated embodiment, the first tri-clamp vessel closure 6010 includes only one insert 6035 providing a single inlet into a chamber 6050 from a source vessel. The second tri-clamp vessel closure 6015 includes a plurality of inserts 6035 that provide a plurality of outlets from the chamber 6050 for distributing a fluid into a plurality of receptacles. With the illustrated configuration, the fluid transfer hub 6000 may be described as a manifold. The chamber 6050 may be bisected by the screen or perforated plate of a corresponding gasket 6020, if applicable.

The inserts 6035 pass through apertures in the bodies 6025 of each tri-clamp vessel closure 6010, 6015, and are connected to the bodies by the cast seal 6030. In addition, in the illustrated embodiments of FIGS. 23 and 24, each insert 6035 is coupled to an optional anchor 6055 that provides an interface between the insert and the body 6025. The tri-clamp vessel closures 6010, 6015 are illustrated with a similar anchor 6055 on each insert 6035, however, a variety of different anchors, or no anchors at all, may also be used. Each anchor 6055 may be any of the types of anchors described above. For example, the anchor 6055 may be in the form of a retaining nut affixed in place around an insert 6035. The retaining nut prevents the insert 6035 from being pulled out of the body 6025. The illustrated anchor 6055 has a retaining nut portion and a cone-shaped portion. The retaining nut portion is located toward the interior of the body 6025, while the cone-shaped section is on the exterior of the body. Further, the anchor 6055 could be a sleeve that prevents the insert 6035 from being pulled out of the body 6025, and provides a surface to which the cast seal 6030 may bond. The anchors 6055 may be constructed of such material that is particularly suitable for bonding with the cast seal 6030, such as metal (aluminum, stainless steel, etc.), plastic, glass-filled plastic, ceramics, and composites. In an embodiment, the anchors 6055 are adhesively attached to the inserts 6035 and combined with the vessel closures 6010, 6015 as discussed above.

FIG. 23 shows a first embodiment of the cast seal 6030. As discussed above, the cast seal 6030 may be a self-leveling silicone that is poured into the body 6025 of each tri-clamp vessel closure 6010, 6015 after the inserts 6035 and optional anchors 6055 are in place. The cast seal 6030 may coat a bottom interior surface of the body 6025. The cast seal 6030 may fill in a seam 6060 between the anchor 6055 and the body 6025 to increase the surface contact with the cast seal and improve the retention of the insert 6035.

FIG. 24 shows a second embodiment of the cast seal 6030. In FIG. 24, the cast seal 6030 includes additional material to coat both the bottom interior surface of the body 6025 as well as the interior sidewalls of each body. The cast seal 6030 is also configured to wrap onto a flange 6065 of the body 6025 to be in contact with the gasket 6020 at tip 6062. In the illustrated embodiment, the tip 6062 of the cast seal 6030, and therefore also the parting seam of the cast seal created by the body 6025 and the cast form (discussed below), is positioned along the top of the flange 6065 and outside of the fluid pathway through the fluid transfer hub 6000. The illustrated positioning of the tip 6062 can help limit any potential for particles of the cast seal 6035 to enter the fluid stream. The cast seal 6030 is also represented with a rounded edge 6068 leading from the chamber 6050 into each insert 6035. The rounded or curved configuration of the edges 6068 reduces the potential for air to become trapped in the chamber 6050 as fluid is transfers across the fluid transfer hub 6000. The curved configuration of the edges 6068 may also improve the flow of fluid exiting the fluid transfer hub 6000 to improve the accuracy of fluid distribution from the hub to the individual receiving vessels, e.g. 5400, FIG. 20.

Figure 25:
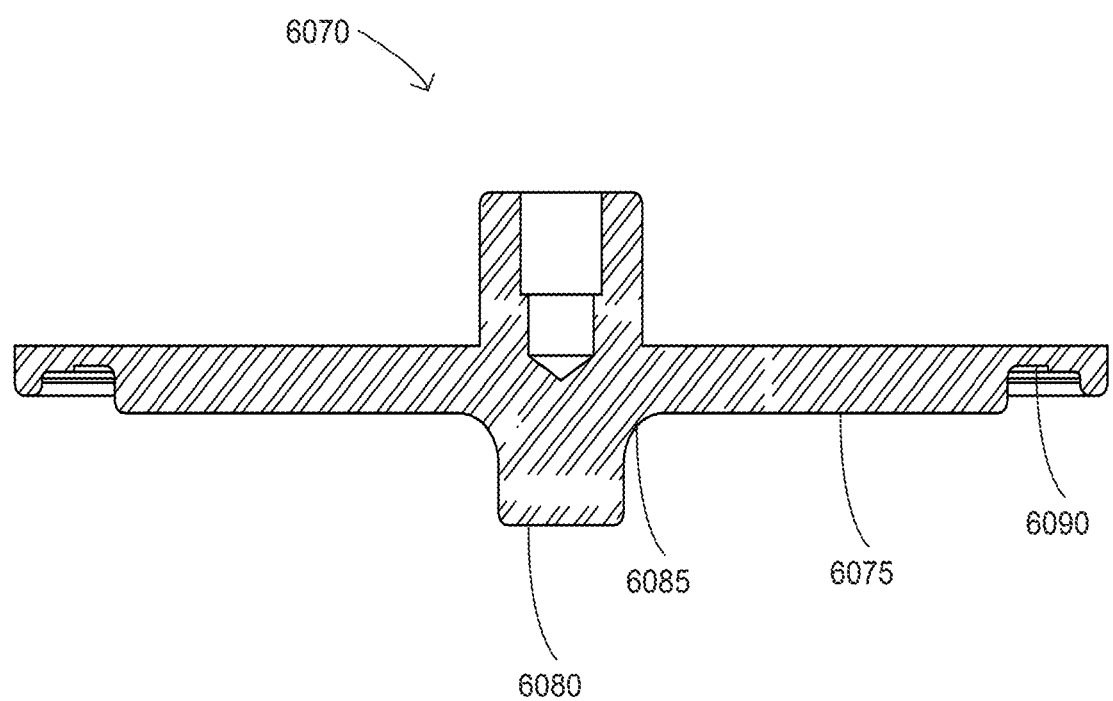
FIG. 25 is a cross-section of a cast form suitable for manufacturing a vessel closure of the fluid transfer hub of FIG. 24.

FIG. 25 shows a cast form 6070 according to one embodiment. The cast form 6070 may be a Teflon® coated aluminum tool. The cast form 6070 includes a base surface 6075 and at least one boss 6080 extending from the base surface 6075. A curved surface 6085 may transition from the base surface 6075 to the boss 6080. The illustrated cast form 6070 may further comprise a circumferential channel 6090 along the flange thereof. The cast form 6070 may also include small holes (not shown) drilled or otherwise provided in communication with the base surface 6075 for providing a fill port and a vent port for use in the casting process as will be understood by one having ordinary skill in the art.

The cast form 6070 of FIG. 25 is particularly suitable for manufacture of the first tri-clamp vessel closure 6010 of the embodiment shown in FIG. 24. The curved surface 6085 of the cast form 6070 is configured to create the rounded edge 6068 leading from the chamber 6050 into each insert 6035 of the first vessel closure 6010. The quantity and arrangement of the at least one boss 6080 on the base surface 6075 is configured to correspond with the quantity and arrangement of apertures in a corresponding body 6025 of a corresponding tri-clamp vessel closure. Further, the circumferential channel 6090 of the cast form 6070 of FIG. 25 provides for the tip 6062 of the cast seal 6030 that wraps onto the flange 6065 of the first tri-clamp vessel closure 6010 of FIG. 24.

The vessel closures may be manufactured by creating one or more apertures in a body. In an embodiment, the apertures may be made using a punch press. However, the apertures may be made using a drill, mill, laser, or any combination thereof. In another embodiment, the apertures are molded when the bodies are molded. Inserts are then inserted axially through the one or more apertures in the body. A casting agent is then cast into the interior of the body. The casting agent is then cured to form a seal around and bond to the one or more inserts. Preferred casting agents include liquid silicone and liquid perfluoropolyether.

In an alternative embodiment, a vessel closure comprising one or more apertures through a body with tubing extending through the one more apertures may be manufactured by first creating a body with one or more apertures. The apertures in the body may be made by the methods mentioned above. Silicone tubing is then inserted through at least one aperture. Thermoplastic tubing is then inserted through at least one other aperture so that the vessel closure has both silicone and thermoplastic tubing. A portion of the thermoplastic tubing is surrounded by a sleeve adhesively attached to the thermoplastic tubing. The sleeve is constructed of material capable of bonding with a casting agent. A casting agent is then cast into the body. In embodiments where the surface of the cast seal is contoured, such as the rise to the tip 6062 or the rounded edge 6068 illustrated in FIG. 24, the step of casting the casting agent into the body may be preceded by obtaining a suitable cast form and engaging the cast form with the body to form a cavity for the casting agent between the body and the cast form. The casting agent is cured to form a seal around and bond to the at least one sleeve surrounding at least a portion of the thermoplastic tubing and to the silicone tubing. In an embodiment, the thermoplastic tubing is C-Flex® tubing. Preferred casting agents include liquid silicone and liquid perfluoropolyether. After curing, the cast form, if present, would be separated from the body.

In the aforementioned methods for manufacturing vessel closures, the liquid silicone may be cast at temperatures much lower than required for insert and/or injection molding. Accordingly, components may be incorporated into the vessel closures that could not be incorporated into vessel closures manufactured using insert and/or injection molding. Such inserts include, but are not limited to, thermoplastic inserts such as C-Flex® tubing. Accordingly, the vessel closures may combine elastomeric and thermoplastic tubing within the same vessel closure. The vessel closures also allow for a variety of different inserts to be included in a single vessel closure, such as a variety of fittings, silicone tubing, C-Flex® tubing, temperature gauges, pH sensors, and others. The vessel closures are low cost and disposable but still capable of effectuating a substantially aseptic seal to a vessel while still allowing maximum flexibility in design. In addition, the methods of utilizing the vessel closures to circulate fluid into and out of a vessel provide systems with relatively few components all while maintaining a substantially aseptic system in which the fluid is located.

The vessel closures may be assembled and then the entire devices or components thereof may be rendered substantially aseptic by, for example, gamma radiation. Alternatively, the entire vessel closures or components thereof may be rendered substantially aseptic by exposure to steam above 121° C. for a period of time long enough to eliminate microorganisms. The entire devices or components thereof may also be rendered aseptic by chemical treatment, such as with ethylene oxide (ETO). Once rendered substantially aseptic, the vessel closures may be appropriately packaged and stored to maintain the substantially aseptic state until ready for use.

The foregoing descriptions of vessel closures, methods of manufacturing vessel closures, and methods of utilizing vessel closures illustrate and describe various embodiments. As various changes can be made in the above embodiments without departing from the scope of the invention disclosed and claimed herein, it is intended that all matter contained in the above description or shown in the accompanying figures shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

The invention claimed is:

1. A fluid distribution hub, comprising:
a first vessel closure having a first body, the first body defining a first aperture extending axially through the first body, the first aperture configured to sealingly attach a first insert to the first body;
a second vessel closure having a second body, the second body defining a second aperture extending axially through the second body and a third aperture extending axially through the second body, the second aperture configured to sealingly attach a second insert to the second body, the third aperture configured to sealingly attach a third insert to the second body;
a gasket arranged between the first vessel closure and the second vessel closure; and
a clamp at least partially surrounding the first vessel closure, the second vessel closure, and the gasket, the clamp securing the first vessel closure to the second vessel closure with the gasket disposed between the first vessel closure and the second vessel closure, a chamber defined between the first vessel closure and the second vessel closure, the gasket bisecting the chamber.

2. The fluid distribution hub according to claim 1, wherein the gasket comprises one of a screen gasket, a perforated plate gasket, and an orifice gasket.

3. The fluid distribution hub according to claim 1, further comprising a first cast seal bonding the first insert to the first aperture and a second cast seal bonding at least one of the second insert to the second aperture or the third insert to the third aperture.

4. The fluid distribution hub according to claim 3, wherein the first cast seal aseptically bonds and seals the first insert to the first aperture the second cast seal aseptically bonds and seals the second insert to the second aperture.

5. The fluid distribution hub according to claim 3, further comprising a third cast seal bonding the third insert to the third aperture, the second cast seal bonding the second insert to the second aperture.

6. The fluid distribution hub according to claim 3, wherein the first cast seal and the second cast seal are formed by a liquid silicone casting agent or perfluorpolyether.

7. The fluid distribution hub according to claim 1, further comprising one or more anchors, each of the one or more anchors adhesively attached to a respective aperture of the second body.

8. The fluid distribution hub according to claim 7, wherein the one or more anchors are constructed from material selected from the group consisting of metal, plastic, glass-filled plastic, ceramics, and composites.

9. The fluid distribution hub according to claim 1, wherein at least one of the first insert, the second insert, or the third insert comprise tubing.

10. The fluid distribution hub according to claim 9, wherein at least one of the first insert, the second insert, or the third insert comprise silicone tubing.

11. The fluid distribution hub according to claim 9, further comprising a sleeve surrounding at least a portion of the second insert or the third insert.

12. The fluid distribution hub according to claim 11, wherein the sleeve is formed of a material having plasticity such that pressure applied to the sleeve causes the sleeve to attach and seal the second insert or the third insert to the respective aperture.

13. The fluid distribution hub according to claim 12, wherein the sleeve is adhesively attached to the second insert or the third insert.

14. The fluid distribution hub according to claim 1, wherein, the gasket fully separates the first vessel closure and the second vessel closure from one another.

15. A fluid distribution hub, comprising:
a first vessel closure having a first body, the first body defining a first aperture extending axially through the first body, the first aperture including a first cast seal configured to sealingly attach a first tube to the first aperture;
a second vessel closure having a second body, the second body defining a second aperture extending axially through the second body and a third aperture extending axially through the second body, the second body including a second cast seal configured to sealingly attach a second tube to the second aperture or a third tube to the third aperture;
a gasket arranged between the first vessel closure and the second vessel closure; and
a clamp at least partially surrounding the first vessel closure, the second vessel closure, and the gasket, the clamp securing the first vessel closure to the second vessel closure with the gasket disposed between the first vessel closure and the second vessel closure.

16. The fluid distribution hub according to claim 15, further comprising:
a first tube sealingly attached to the first aperture by the first cast seal;
a second tube sealingly attached to the second aperture by the second cast seal; and
a third tube sealingly attached to the third aperture.

17. The fluid distribution hub according to claim 16, wherein the first cast seal aseptically bonds and seals the first tube to the first aperture the second cast seal aseptically bonds and seals the second tube to the second aperture.

18. A method of manufacturing a fluid distribution hub, the method comprising:
positioning a gasket between a first vessel closure and a second vessel closure such that the gasket bisects a chamber defined between the first vessel closure and the second vessel closure, the first vessel closure having a first body, the first body defining a first aperture extending axially through the first body and a first insert sealingly attached to the first aperture, the second vessel closure having a second body, the second body defining a second aperture extending axially through the second body and a third aperture extending axially through the second body, the second vessel closure including a second insert sealingly attached to the second aperture and a third insert sealingly attached to the third aperture; and securing the first vessel closure to the second vessel closure with a clamp at least partially surrounding the first vessel closure, the second vessel closure, and the gasket.

19. The method of manufacturing according to claim 18, further comprising creating the first vessel closure including bonding the first insert to the first aperture with a cast seal.

20. The method of manufacturing according to claim 18, further comprising creating the second vessel closure including bonding the second insert to the second aperture or the third insert to the third aperture with a cast seal.

* * * * *